(12) United States Patent
Kempe

(10) Patent No.: US 6,652,721 B2
(45) Date of Patent: Nov. 25, 2003

(54) SENSOR FOR DETERMINATION OF $O_2$ CONCENTRATION IN LIQUIDS

(75) Inventor: Eberhard Kempe, Berlin (DE)

(73) Assignee: Biotechnologie Kempe GmbH (DE)

( * ) Notice: Subject to any disclaimer, the term of this patent is extended or adjusted under 35 U.S.C. 154(b) by 25 days.

(21) Appl. No.: 09/961,921

(22) Filed: Sep. 24, 2001

(65) Prior Publication Data

US 2002/0036136 A1 Mar. 28, 2002

(30) Foreign Application Priority Data

Sep. 25, 2000 (DE) .......................... 100 47 708

(51) Int. Cl.[7] .............................................. G01N 27/26
(52) U.S. Cl. .................... 204/412; 204/408; 204/409; 204/272; 205/782
(58) Field of Search ................. 204/412, 415, 204/431, 432, 435, 409

(56) References Cited

U.S. PATENT DOCUMENTS

| | | | | |
|---|---|---|---|---|
| 2,768,135 A | * | 10/1956 | Adelson | |
| 2,805,191 A | * | 9/1957 | Hersch | |
| 3,003,932 A | * | 10/1961 | Frey et al. | |
| 3,518,179 A | * | 6/1970 | Bleak et al. | |
| 4,092,233 A | * | 5/1978 | Clemens et al. | |
| 4,152,233 A | * | 5/1979 | Chand | |
| 4,207,161 A | | 6/1980 | Pegnim | |
| 4,227,974 A | * | 10/1980 | Petersen et al. | |
| 5,273,631 A | * | 12/1993 | Ohsawa et al. | |
| 5,527,444 A | | 6/1996 | Sweeney, Jr. | |

FOREIGN PATENT DOCUMENTS

| | | |
|---|---|---|
| CH | 618 515 | 7/1980 |
| DE | 301 930 | 7/1994 |
| DE | 43 42 787 C1 | 7/1995 |
| WO | 83/04095 | 11/1983 |
| WO | 96/05509 | 2/1996 |

\* cited by examiner

Primary Examiner—T. Tung
(74) Attorney, Agent, or Firm—McGlew and Tuttle, P.C.

(57) ABSTRACT

A sensor (1) for measuring $O_2$ concentrations in liquids (2) has a working electrode (3), with a counterelectrode (4) and with a reference electrode (5), wherein the working electrode (3) and the counterelectrode (4) are in contact with the liquid (2). The reference electrode (5) is separated from the liquid (2) by a diaphragm (6). The reference electrode (5) measures a polarization voltage effectively acting at the working electrode (3) and is connected to a potentiostat regulating the potential between the working electrode (3) and the counterelectrode (4). The reference electrode (5), the working electrode (3) and the counterelectrode (4) are arranged coaxially to one another, wherein the working electrode (3) and the counterelectrode (4) are arranged around the reference electrode (5).

18 Claims, 4 Drawing Sheets

SENSOR FOR DETERMINATION OF $O_2$ CONCENTRATION IN LIQUIDS

FIELD OF THE INVENTION

The present invention pertains to a sensor for measuring $O_2$ concentrations in liquids, with a working electrode, with a counterelectrode and with a reference electrode, wherein the working electrode and the counterelectrode are in contact with the liquid, wherein the reference electrode is separated from the liquid via a diaphragm and wherein the reference electrode measures a polarization voltage effectively acting at the working electrode and is connected to a potentiostat regulating the potential between the working electrode and the counterelectrode.

BACKGROUND OF THE INVENTION

Oxygen in the molecular form, dissolved in liquids, is undesirable in many chemical and/or food technological processes. For example, very low oxygen concentrations are necessary for reasons of purity and/or corrosion protection in the manufacture of semiconductors or in the water-steam cycle in power plants. Low oxygen contents are desirable in food technology for reasons of good shelf life. For example, only very little oxygen may be present in the end product at most in the area of beer-brewing if satisfactory stability of the taste is to be achieved. The accurate measurement and monitoring of oxygen concentrations is therefore of broad analytical significance.

A sensor of the design mentioned in the introduction has been known from the reference source *Brauindustrie*, 3/88. This is a three-electrode sensor operating by amperometric measurement with a working electrode, a counterelectrode as well as a reference electrode. The working electrode and the counterelectrode are arranged coaxially to one another and the liquid flows through the intermediate space between the working electrode and the counterelectrode. The reference electrode is arranged on the side and is connected via a diaphragm passing through the reference electrode.

The basic functions of the sensor known so far and also of a sensor according to the present invention are as follows. An electric current between the cathodically polarized working electrode and the counterelectrode, which results from the reduction of $O_2$ molecules at the working electrode, is measured. It is obvious that reduction of $O_3$ molecules can also take place and the sensors known so far, just as a sensor according to the present invention, can be used to determine ozone or total (molecular) oxygen. On the one hand, accurate setting of the potential between the working electrode and the counterelectrode is necessary for the measurement of the current intensity. On the other hand, determination of the rate of flow of the liquid must be performed if the measurement is to be performed in flowing liquids, because the measured values obtained are also determined by the thickness of the boundary layer at the working electrode in which the $O_2$ transport takes place in a diffusion-controlled manner. The thickness of the boundary layer is in turn a function of the rate of flow.

A method for determining the rate of flow is, e.g., the technique known from practice in which two NTC resistors are used. One NTC resistor is heated and is arranged in the flow of the liquid. The second NTC resistor is likewise arranged in the liquid, but in an area without flow or only low flow. The second NTC resistor is used as a compensating resistor concerning the temperature of the liquid, while the voltage drop over the first NTC resistor (in case of temperature compensation) is an indicator of the "cooling effect" of the flowing liquid and therefore also of the rate of flow. It is obvious that the amount of liquid is so large that no appreciable increase in the temperature of the liquid takes place as a whole due to the heating of the first NTC.

In conjunction with a potentiostat, the reference electrode ensures that the electrochemical conditions are maintained at a constant value between the working electrode and the counterelectrode. A suitable circuit can be found, e.g., in the reference source *Handbuch der industriellen Meβtechnik* [Handbook of Industrial Measuring Technique], 6th edition, 1994, R. Oldenbourg Verlag, Munich, Vienna, p. 1102.

One disadvantage of a sensor according to the above-mentioned state of the art is that it has a protruding design. Due to the fact that the working electrode and the counterelectrode, on the one hand, and the reference electrode, on the other hand, are arranged side by side, there also arises a disturbing effort to contact the sensor as a whole. In addition, a compact conductor system is necessary, which leads to a relatively great pressure drop and a considerable risk for microbial contamination. In addition, sterilization is cumbersome.

SUMMARY AND OBJECTS OF THE INVENTION

The basic technical object of the present invention is to provide a sensor of the design mentioned in the introduction, which has a compact design, has a reduced risk for microbial contamination and can be sterilized in a simple manner.

To accomplish this object, the present invention teaches that the reference electrode, the working electrode and the counterelectrode are coaxial to one another, the working electrode and the counterelectrode being arranged around the reference electrode. In other words, the sensor has an essentially rotationally symmetrical design, with the reference electrode forming the middle part.

The liquid can be easily passed through between the working electrode and the counterelectrode or past the working electrode and the counterelectrode, without the need for longer lines of a narrow cross section. The system can be rather designed as an open system, e.g., as a cylindrical system, wherein the liquid can flow through at least one front surface of the cylinder which is open over its full area.

A very compact design is obtained with the present invention due to the coaxial arrangement of all electrodes. Other advantages are a small pressure drop, reduced risk for microbial contamination, simpler sterilizability, simpler manufacturability, and reduced maintenance requirement.

When viewed in the radial direction, the working electrode and the counterelectrode may follow each other, in principle, in any desired arrangement. The counterelectrode is preferably arranged around the working electrode. The working electrode or the counterelectrode may form an outer wall of the reference electrode and thus form a structural unit.

The electrodes may have, in principle, any shape, e.g., a square shape relative to their cross section at right angles to the axis. However, the counterelectrode and/or the working electrode are preferably of a cylinder jacket design, i.e., they have a circular cross section for manufacturing technical reasons.

The reference electrode is, e.g., a class 2 electrode with constant input potential, preferably an Ag/AgCl electrode. The material of the working electrode may be silver or a silver alloy. The material of the counterelectrode may be a stainless steel.

All electrical contacts for the connection of the working electrode, the counterelectrode and the reference electrode may be arranged at one end of the axis of the sensor. As a result, simple contactability and higher electrical reliability are achieved.

A coaxial opening, through which the liquid can flow, preferably a coaxial opening extending over the entire cross section of the sensor, may be arranged at the end of the axis of the sensor located opposite the contacts. In conjunction herewith, a radial opening, through which the liquid can flow, may be arranged in the electrode that is the outermost electrode in the radial direction. For example, liquid can be passed through the radial opening into the interior of the sensor, and the coaxial opening functions as an outflow opening in this case. If the electrical contacts are not arranged in the area of one end of the axis of the sensor (but, e.g., laterally or radially), a coaxial opening of the above-mentioned design each may be arranged at both ends. An extremely low flow resistance is achieved in this case.

A temperature sensor, which is in thermal contact with the liquid, preferably an NTC resistor, may be arranged between the counterelectrode and the working electrode, i.e., in the intermediate space of the sensor through which the liquid flows. This temperature sensor can be used solely to measure the temperature of the liquid, e.g., within the framework of a temperature compensation of an arrangement for measuring a rate of flow, but it may also be used itself to measure the rate of flow through the sensor (with or without external temperature compensation). It is, of course, also possible to use other devices for measuring rates of flow. The examples include pressure drop measurement over a standard diaphragm, a standard nozzle or a venturi tube, the float element method, turbine flow meters, impeller flow meters, oval wheel flow meters, ultrasonic flow meters and flow measurement by magnetic induction.

The other designs described below are of significance in themselves. The additional elements described may represent, on the one hand, an (external) calibrating means for calibrating a sensor of the above-described design. However, the overall design obtained can also be used as a sensor, in which case there is a possibility for "in situ" calibration.

A venturi nozzle may be connected to the coaxial opening. A flow chamber with an opening through which the liquid can flow, which is preferably designed as a second radial opening, may be connected on the side of the venturi nozzle located opposite the coaxial opening. The flow chamber may include an electrolysis cell. A heatable temperature sensor, preferably an NTC resistor, may be arranged for flow measurement or for the measurement of the rate of flow in the area of the venturi nozzle. However, this may also be determined, e.g., from the pressure drop.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
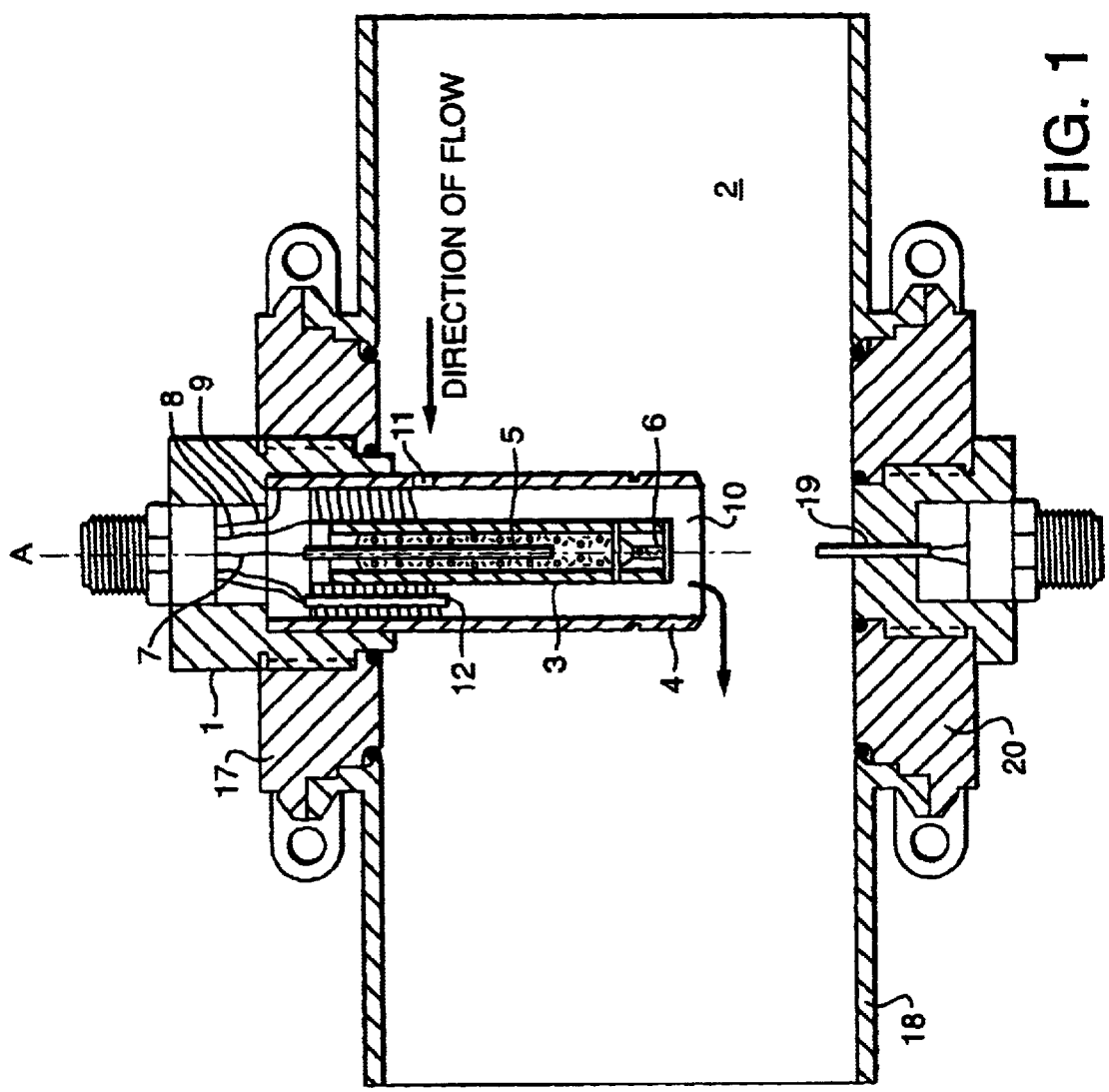
FIG. 1 is a sectional view of an exemplary embodiment of the sensor which has an especially simple design.
Figure 2:
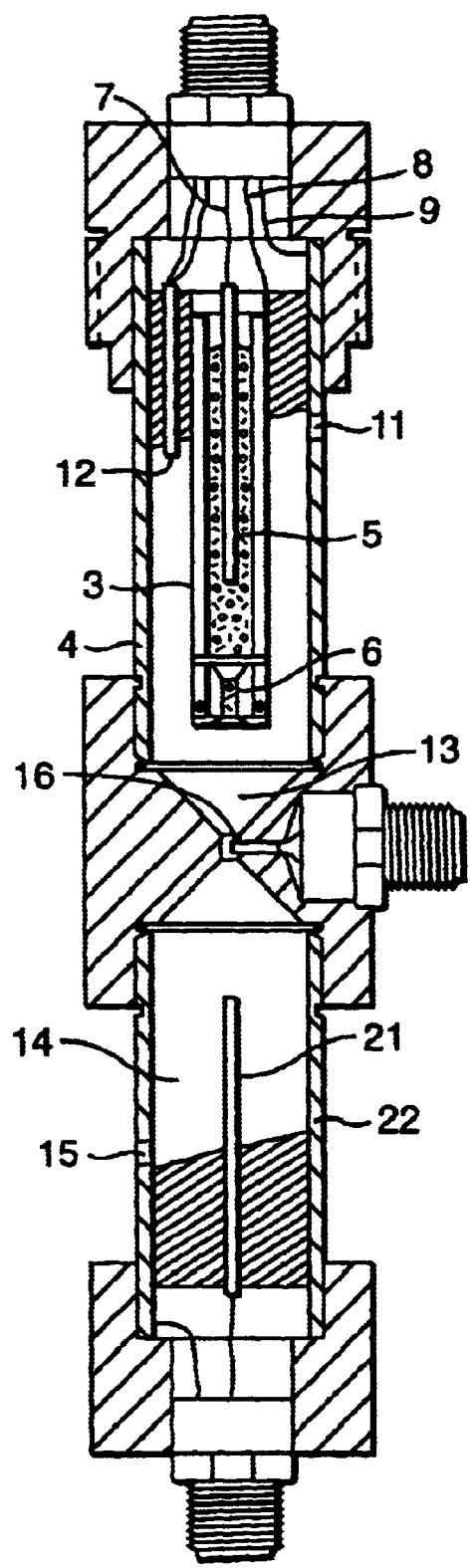
FIG. 2 is a sectional view of a sensor with calibration possibility.

Referring to the drawings in particular, a sensor 1 for measuring $O_2$ concentrations in liquid 2, with a working electrode 3, with a counterelectrode 4 and with a reference electrode 5 can be recognized in the two FIGS. 1 and 2, wherein the working electrode 3 and the counterelectrode 4 are in contact with the liquid 2 and wherein the reference electrode 5 is separated from the liquid 2 by a diaphragm 6, wherein the reference electrode 5 measures a polarization voltage effectively acting at the working electrode 3 and is connected to a potentiostat regulating the potential between the working electrode 3 and the counterelectrode 4. The reference electrode 5, the working electrode 3 and the counterelectrode 4 are arranged coaxially to one another, the working electrode 3 and the counterelectrode 4 being arranged coaxially around the reference electrode 5. The counterelectrode 4 is arranged specifically around the working electrode 3. The counterelectrode 4 and the working electrode 3 have a cylinder jacket design.

The reference electrode 5 is a class 2 electrode with constant self-potential, namely, an Ag/AgCl electrode. The material of the working electrode 3 is silver and the material of the counterelectrode 4 is stainless steel. All electrical contacts 7, 8, 9 for the connection of the working electrode 3, the counterelectrode 4 and the reference electrode 5 are arranged at one end of the axis A of the sensor 1. A coaxial opening 10, through which the liquid 2 can flow, is arranged at the end of the axis A of the sensor 1 which is located opposite the contacts 7, 8, 9. A radial opening 11, through which the liquid 2 can flow, is arranged in the counterelectrode 4. A temperature sensor 12, which is in thermal contact with the liquid 2, namely, an NTC resistor, is arranged between the counterelectrode 4 and the working electrode 3. It is arranged such that the NTC resistor is arranged in a partial area of the intermediate space between the working electrode 3 and the counterelectrode 4, in which there is practically no flow of liquid. This NTC resistor is used to measure the temperature of the liquid or to compensate the temperature within the framework of measures taken to measure the rate of flow.

It can also be recognized in FIG. 1 that the sensor 1 is installed in a pipeline 18 by means of a flange. The orientation is selected to be such that the axis A of the sensor 1 is at right angles to the direction of flow of the liquid 2. The liquid 2 flows from right to left in the pipeline 18. The flow therefore arrives at the radial opening 11 and the liquid 2 passes through it into the interior of the sensor 1, namely, between the working electrode 3 and the counterelectrode 4. Due to the pressure of the arriving flow of the liquid 2, a partial amount of the liquid 2 is thus transported through the sensor 1 and is again discharged through the axial opening 10. The axial opening 10 is directed with its cross section in parallel to the direction of flow of the liquid 2. Furthermore, another NTC resistor 19 can be recognized, which is installed in the pipeline 18 by means of another flange 20. At least part of the NTC resistor 19 immerses into the flowing liquid next to the sensor 1 and away from the sensor 1. This NTC resistor 19 is heated and is used to determine the rate of flow. Even though the rate of flow in the sensor 1 is not determined directly by this arrangement, but the rate of flow in the pipeline 18, the latter is in a defined mathematical relationship with the rate of flow through the sensor 1 due to the fixed arrangement of the sensor 1, because the flow resistance through the sensor 1 remains practically unchanged under different hydrodynamic conditions typical of the use.

FIG. 2 shows a variant which can be used to calibrate an expanded sensor 1 according to FIG. 1, but which may also be used as a sensor 1, e.g., within the framework of a bypass to a pipeline 18 as a whole, with the possibility of in situ calibration. A venturi nozzle 13 is connected to the coaxial opening 10. A flow chamber 14 with an opening 15, which is preferably designed as a second radial opening 15 and through which the liquid 2 can flow, is connected on the side of the venturi nozzle 13 located opposite the coaxial opening 10. The flow chamber 14 is designed as an electrolysis cell with a separating electrode 21 and a counterelectrode 22. Molecular oxygen can be separated at the separating electrode 21 by water electrolysis by applying a voltage between the separating electrode 21 and the counterelectrode 22. The counterelectrode 22 is galvanically separated from the counterelectrode 4, e.g., by making the venturi nozzle 13 from a preferably high temperature-resistant polymer (100° C., preferably 120° C. or higher; e.g., PE, PP, PC or PET). A heatable NTC resistor 16 is arranged in the area of the venturi tube 13.

The probe according to FIG. 2 is connected in the normal operation such that the radial opening 15 is an inlet opening and the radial opening 11 is an outlet opening. The separating electrode 21 and the counterelectrode 22 carry no potential in the normal operation, i.e., no oxygen is separated. The liquid flows through the electrolysis cell or the flow chamber 14 as well as the venturi nozzle into the area between the working electrode 3 and the counterelectrode 4, where the oxygen content is determined in the above-described manner. The NTC resistor 16 is used to determine the rate of flow. If calibration is to be performed, this can be carried out, assuming constant oxygen content in the liquid, without any interruption or expansion, namely, by simply applying a suitable electrolysis voltage to the separating electrode. The rate of formation of molecular oxygen can be determined from the current intensity now flowing, and this rate of formation determines the oxygen concentration in the liquid flowing through the arrangement, which becomes established and is increased by a defined extent, in conjunction with the rate of flow. It is particularly advantageous in connection with the venturi nozzle 13 that the liquid 2 is mixed practically homogeneously with the oxygen formed, without the need for complicated mixers which are difficult to sterilize. The necessary calibration parameters can be determined and set based on the increase in the values measured at the working electrode 3 in conjunction with the current intensity at the separating electrode 21. The potential is then again removed from the separating electrode 21.

The sensor 1 according to the present invention is advantageously designed in terms of the selection of the materials used such that sterilization with steam can be carried out at, e.g., 120° C. and higher without damage and without disassembly.

Figure 3:
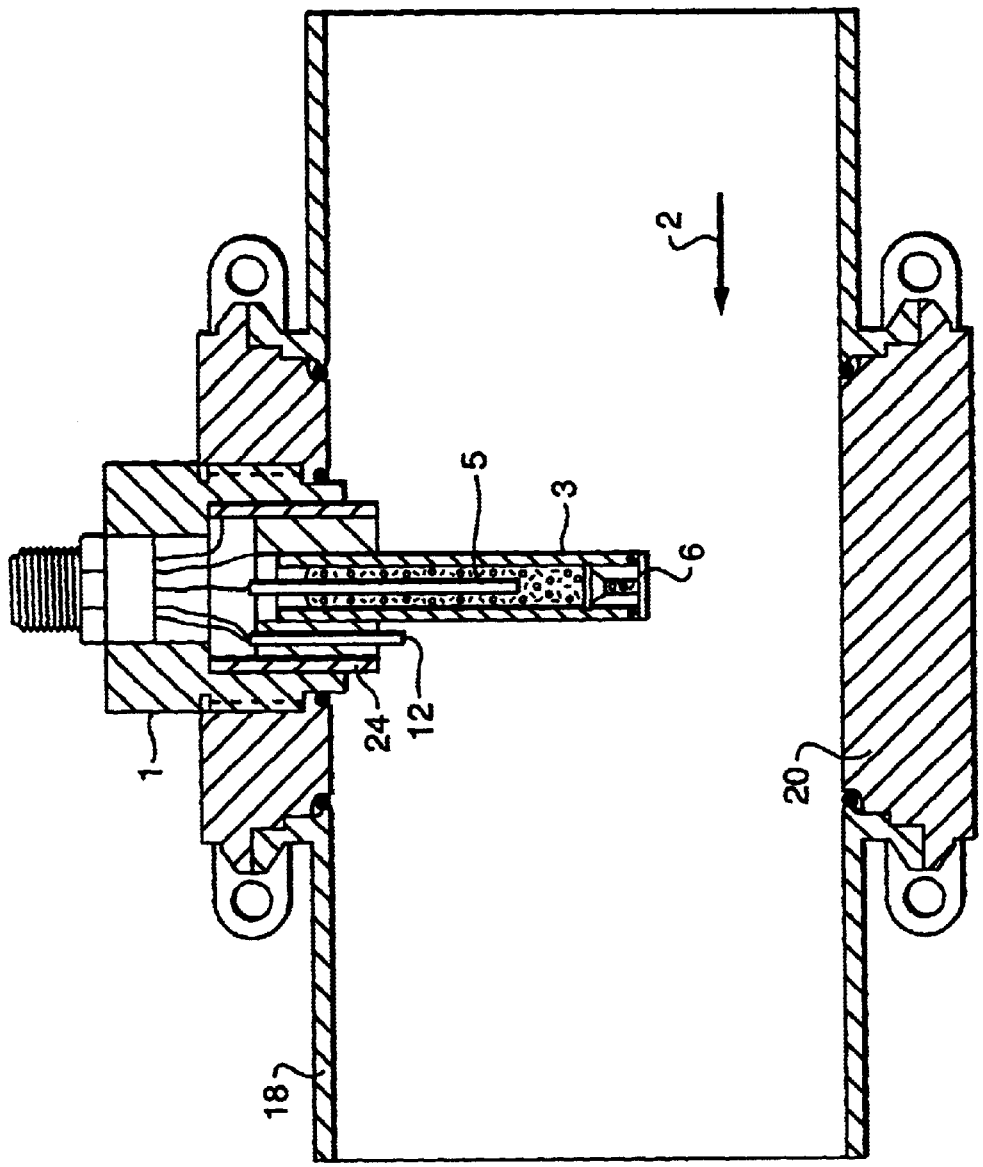
FIG. 3 is a sectional view of a sensor with directly arriving flow in an alternative embodiment compared with the sensor according to FIG. 1.

In the embodiment of the sensor 1 according to FIG. 1 which is shown in FIG. 3, the counterelectrode 24 is substantially shorter than the counterelectrode 4 according to FIG. 1, whereas the working electrode 3, the reference electrode 5, the diaphragm 6 and the NTC temperature sensor 12 have the same length as in the sensor according to FIG. 1. The opposite NTC resistor 19 according to FIG. 1 is not present in the embodiment of the sensor according to FIG. 3.

Based on the shortened design of the counterelectrode 24, the liquid 2 in the pipeline 18 flows directly around the working electrode 3 over nearly its full length and the annular space present between the long counterelectrode 4 and the working electrode 3 in the sensor 1 according to FIG. 1 is absent. The risk for microbial contamination in the flow space within the relatively long counterelectrode 4 of the sensor 1 according to FIG. 1, which counterelectrode is provided with the radial opening 11, is thus no longer present in the embodiment of the sensor 1 with the shortened counterelectrode 24 according to FIG. 3.

The absence of the second NTC resistor 19 in the sensor 1 according to FIG. 3 requires a different flow measurement method than with FIG. 1.

Figure 5:
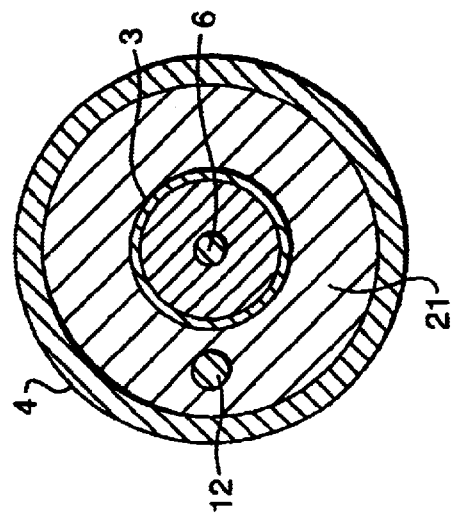
FIG. 5 is a front view of the sensor according to FIG. 4.
Figure 4:
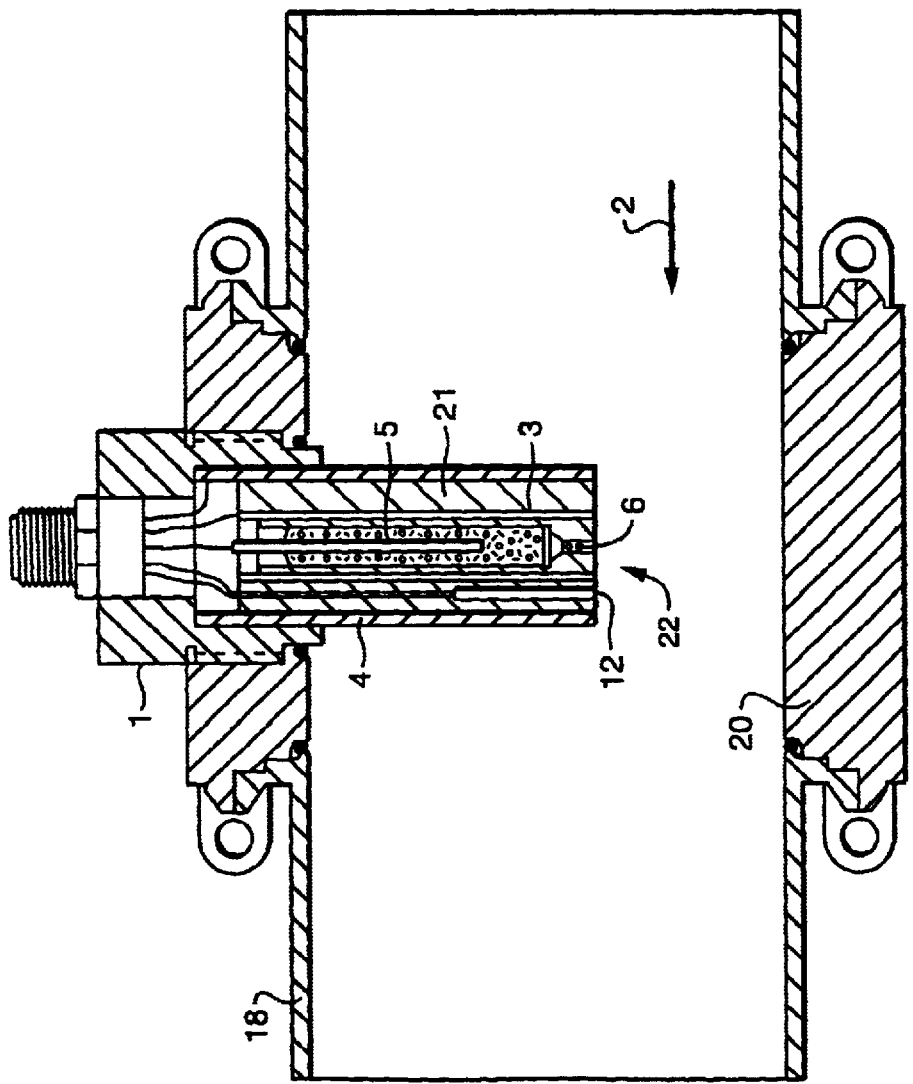
FIG. 4 is a sectional view of another sensor with directly arriving flow in an alternative embodiment compared with the sensor according to FIG. 1.

In another embodiment of the sensor 1 according to FIGS. 4 and 5, which likewise show an alternative embodiment of the sensor 1 according to FIG. 1, the cylinder jacket-shaped working electrode 3 and the likewise cylinder jacket-shaped counterelectrode 4 as well as the diaphragm 6 and the NTC temperature sensor 12 end flush in a common front surface 22 of the sensor 1, wherein the annular intermediate space 21 between the working electrode 3 and the counterelectrode 4 is filled with a plastic. The front surface 22 thus forms the active electrode surface at the front surface of the sensor 1, as is shown in the front view in FIG. 5. The flow of the liquid 2 in the pipeline 18 thus wets only the front surface 22 as a common end face of the working electrode 3, the counterelectrode 4, the diaphragm 6 and the NTC temperature sensor 12. The active surface of the sensor 1, which is swept by the liquid 2, is substantially smaller here than in the embodiments of the sensor 1 according to FIG. 1 and FIG. 3.

The opposite second NTC resistor 19 is absent in this embodiment as well, so that a different flow measurement method must also be used here than in the sensor according to FIG. 1.

While specific embodiments of the invention have been shown and described in detail to illustrate the application of the principles of the invention, it will be understood that the invention may be embodied otherwise without departing from such principles.

What is claimed is:

1. A sensor for measuring $O_2$ concentrations in liquids, the sensor comprising:

a working electrode;

a counterelectrode;

a reference electrode, said working electrode and said counterelectrode are in contact with the liquid;

a potentiostat regulating a potential between said working electrode and said counterelectrode;

a diaphragm, said reference electrode being separated from said liquid by said diaphragm, said reference electrode measuring a polarization voltage effectively acting at said working electrode and being connected to said potentiostat, said reference electrode, said working electrode and said counterelectrode being arranged coaxially to one another with said working electrode and said counterelectrode being arranged around said reference electrode;

contacts, for a connection of said working electrode, said counterelectrode and said reference electrode arranged at one axial end of the sensor;

a coaxial opening through which the liquid can flow arranged at an axial end of said axis of said sensor opposite said contacts;

a radial opening through which the liquid can flow arranged in a radially outermost one of said working electrode, said counterelectrode and said reference electrode.

2. A sensor in accordance with claim 1, wherein said counterelectrode is arranged around said working electrode.

3. A sensor in accordance with claim 1, wherein said counterelectrode and/or said working electrode have a cylinder jacket design.

4. A sensor in accordance with claim 1, wherein said reference electrode is a class 2 electrode with constant self-potential.

5. A sensor in accordance with claim 1, wherein said reference electrode is an Ag/AgCl electrode.

6. A sensor in accordance with claim 1, wherein the material of said working electrode is silver.

7. A sensor in accordance with claim 1, further comprising:

a temperature sensor in thermal contact with the liquid including a NTC resistor, is arranged between said counterelectrode and said working electrode.

8. A sensor in accordance with claim 7, wherein said working electrode, said counterelectrode, said diaphragm and said temperature sensor end flush in a front surface of the sensor, wherein an annular intermediate space between said counterelectrode and said working electrode is filled with a plastic.

9. A sensor in accordance with claim 1, wherein a venturi nozzle is connected to said coaxial opening.

10. A sensor in accordance with claim 9, further comprising:

a flow chamber, with an opening as a radial opening through which liquid can flow, is connected on a side of said venturi nozzle located opposite said coaxial opening.

11. A sensor in accordance with claim 10, wherein said flow chamber includes an electrolysis cell.

12. A sensor in accordance with claim 9, wherein a heatable temperature sensor including an NTC resistor, is arranged in an area of said venturi nozzle.

13. A sensor in accordance with claim 1, wherein an axial length of said counterelectrode is shorter than an axial length of said working electrode, a liquid within a pipeline to which the sensor is connected flows directly around said working electrode.

14. A sensor in accordance with claim 1, wherein the material of said counterelectrode is stainless steel.

15. A sensor for measuring oxygen concentration in a liquid, the sensor comprising:

a reference electrode;

a diaphragm separating said reference electrode from the liquid;

a working electrode arranged in contact with the liquid and around said reference electrode;

a counter electrode arranged in contact with the liquid and around said reference electrode, said counter electrode being spaced from said working electrode to define a liquid flow path for flowing of the liquid between said working electrode and said counter electrode;

a potentiostat regulating a potential between said working electrode and said counter electrode, said potentiostat being connected to said reference electrode and measuring a polarization voltage effectively acting at said working electrode.

16. A sensor in accordance with claim 15, wherein:

one axial end of said working electrode and said counter electrode define a coaxial opening in communication with said liquid flow path between said working electrode and said counter electrode, said coaxial opening also being in communication with a surrounding environment;

a radially outermost one of said working electrode and said counter electrode defines a radial opening in communication with said liquid flow path between said working electrode and said counter electrode, said radial opening also being in communication with the surrounding environment, said radial opening being arranged spaced from said one axial end.

17. A sensor in accordance with claim 16, wherein:

electrical contacts are arranged on said working electrode, said counter electrode and said reference electrode at another axial end of said electrodes diametrically opposite said one axial end.

18. A sensor in accordance with claim 15, wherein:

said reference electrode, said working electrode and said counter electrode are substantially coaxial.

* * * * *